US012478497B2

(12) United States Patent
Hall

(10) Patent No.: US 12,478,497 B2
(45) Date of Patent: Nov. 25, 2025

(54) WATERPROOF CUSTOMIZABLE APPENDAGE SPLINTING KIT

(71) Applicant: Diana Hall, Pueblo, CO (US)

(72) Inventor: Diana Hall, Pueblo, CO (US)

( * ) Notice: Subject to any disclaimer, the term of this patent is extended or adjusted under 35 U.S.C. 154(b) by 360 days.

(21) Appl. No.: 18/185,816

(22) Filed: Mar. 17, 2023

(65) Prior Publication Data

US 2023/0293332 A1 Sep. 21, 2023

Related U.S. Application Data

(60) Provisional application No. 63/321,452, filed on Mar. 18, 2022.

(51) Int. Cl.
*A61F 5/058* (2006.01)

(52) U.S. Cl.
CPC ...... *A61F 5/05866* (2013.01); *A61F 5/05825* (2013.01)

(58) Field of Classification Search
CPC .............. A61F 5/05866; A61F 5/05825; A61F 5/05841; A61F 5/05858; A61F 5/058; A61F 5/05; A61F 5/04; A61F 5/01; A61F 5/00; A61F 5/05816; A61F 5/05833; A61F 5/042; A61F 5/37
See application file for complete search history.

(56) References Cited

U.S. PATENT DOCUMENTS 3,788,307 A * 1/1974 Kistner ............... A61F 5/05866 473/62
6,913,582 B2 * 7/2005 Chen .................. A61F 5/05866 602/5

* cited by examiner

*Primary Examiner* — Tarla R Patel
(74) *Attorney, Agent, or Firm* — Plumsea Law Group, LLC

(57) ABSTRACT

Customizable split kits are provided including a plurality of components that may be assembled into a waterproof and breathable wrist splint. The splint assembled from the kit can fit multiple size/shaped arms or other appendages, is moldable for custom positioning, protective, immobilizing, and locks-on for compliance.

18 Claims, 11 Drawing Sheets

WATERPROOF CUSTOMIZABLE APPENDAGE SPLINTING KIT

CROSS REFERENCE TO RELATED APPLICATIONS

This application claims priority to U.S. provisional application 63/321,452 entitled "Waterproof Customizable Wrist Splinting Kit" and filed Mar. 18, 2022, the disclosure of which is hereby incorporated by reference in its entirety.

BACKGROUND

1. Field of the Disclosure

The present disclosure relates to splints, casts, and other medical immobilization devices for treating breaks, sprains, Carpal Tunnel Syndrome and other injuries and chronic conditions requiring immobilization of a human appendage.

2. Description of Related Art

A variety of splits and casts are known in the art of medical devices. Such devices are commonly used to immobilize a part of a human body in order to allow the body to heal, such as after a bone fracture or joint sprain—or to avoid surgery or relieve pain by immobilizing and supporting a joint.

Existing splits and casts are generally deficient in one or more ways that may affect the comfort, usability, durability, fit, or other aspects of the immobilization apparatus. For example, traditional field splints (like SAM splints) are not breathable and not rigid enough to immobilize under pressure. They can deform and are not fitted to the wearer's bodily shape. Splints commonly put on in Emergency Rooms or Urgent Care facilities are not waterproof or washable, so patients cannot wash their hands or shower—basic hygiene needs. And they don't lock-on, so patients can be non-compliant with them and put themselves at risk of further injury or bone displacement. They trap moisture and bacteria against the skin, which can cause imaceration. The skin cannot be observed while immobilized, so infections may not be caught right away.

Accordingly, there is a need in the art for splints that are waterproof, breathable, washable, and hygienic that can fit a variety of body sizes and shapes.

SUMMARY OF THE INVENTION

In one aspect, the disclosure provides a kit for assembling a waterproof wrist splint, comprising: a back spine, configured to extend along a back side of a wearer's forearm and hand; a front spine, configured to extend along a front side of the wearer's forearm and hand; each of the back spine and the front spine respectively including a plurality of attachment structures therein on an outer surface thereof; a pair of palm beads, configured to fit on opposite sides of the wearer's hand; a pair of wrist beads, configured to fit on opposite sides of the wearer's wrist; at least one pair of forearm beads, each of the pair of forearm beads configured to fit on opposite sides of the wearer's forearm; each of the palm beads, wrist beads, and forearm beads including a through-hole extending from a first side to a second side thereof; and a plurality of cable ties, each of the plurality of cable ties being configured to extend through the through-hole in one of the respective palm beads, wrist beads, and forearm beads and into the attachment structures on one or more of the back spine and the front spine, so as to form a customizable sized splint.

In another aspect, this disclosure provides a customizable sized splint for immobilizing a portion of a wearer's body, comprising: a first spine, configured to extend along a first side of the wearer's limb; a second spine, configured to extend along a second side of the wearer's limb, the second side of the wearer's limb being opposite the first side of the wearer's limb; each of the first spine and the second spine respectively including a plurality of attachment structures therein on an outer surface thereof; a plurality of sets of beads, each set of beads being configured to partially surround a portion of the wearer's limb, each bead in the plurality of sets of beads including a through-hole therein; and a plurality of cables ties, each cable tie connecting the bead in each respective set of beads to the first spine and the second spine by extending through the through-hole in each bead and connecting to another cable tie at the attachment structure, the plurality of cable ties thereby connecting the first spine to the second spine so as to immobilize the wearer's limb therebetween.

In another aspect, this disclosure provides a kit for assembling a waterproof wrist splint, comprising: a back spine, the back spine including a first waterproof closed-cell foam layer on an inner surface thereof; a front spine, the front spine including a second waterproof closed-cell foam layer on an inner surface thereof; each of the back spine and the front spine respectively including a plurality of attachment structures therein on an outer surface thereof; a plurality of sets of beads, each set of beads being configured to partially surround a portion of the wearer's limb, each bead in the plurality of sets of beads including a through-hole therein and each bead in the plurality of sets of beads including a waterproof closed-cell foam layer on an inner surface thereof; and a plurality of cable ties, each of the plurality of cable ties being configured to extend through the through-hole in one of the beads in each of the plurality of sets of beads and into the attachment structures on each of the back spine and the front spine, so as to form a customizable sized splint.

Other systems, methods, features and advantages of the disclosure will be, or will become, apparent to one of ordinary skill in the art upon examination of the following figures and detailed description. It is intended that all such additional systems, methods, features and advantages be included within this description and this summary, be within the scope of the disclosure, and be protected by the following claims.

BRIEF DESCRIPTION OF THE DRAWINGS

The disclosure can be better understood with reference to the following drawings and description. The components in the figures are not necessarily to scale, emphasis instead being placed upon illustrating the principles of the disclosure. Moreover, in the figures, like reference numerals designate corresponding parts throughout the different views.

DETAILED DESCRIPTION

The purpose of this disclosure is to provide a waterproof, breathable, washable, hygienic wrist field splint that can fit multiple size/shaped appendages, is moldable for custom positioning, protective, immobilizing, and locks-on for compliance. The splint of this disclosure also takes less time to apply than e.g. a fiberglass cast, as no drying time or cast saws are needed.

Figure 1:
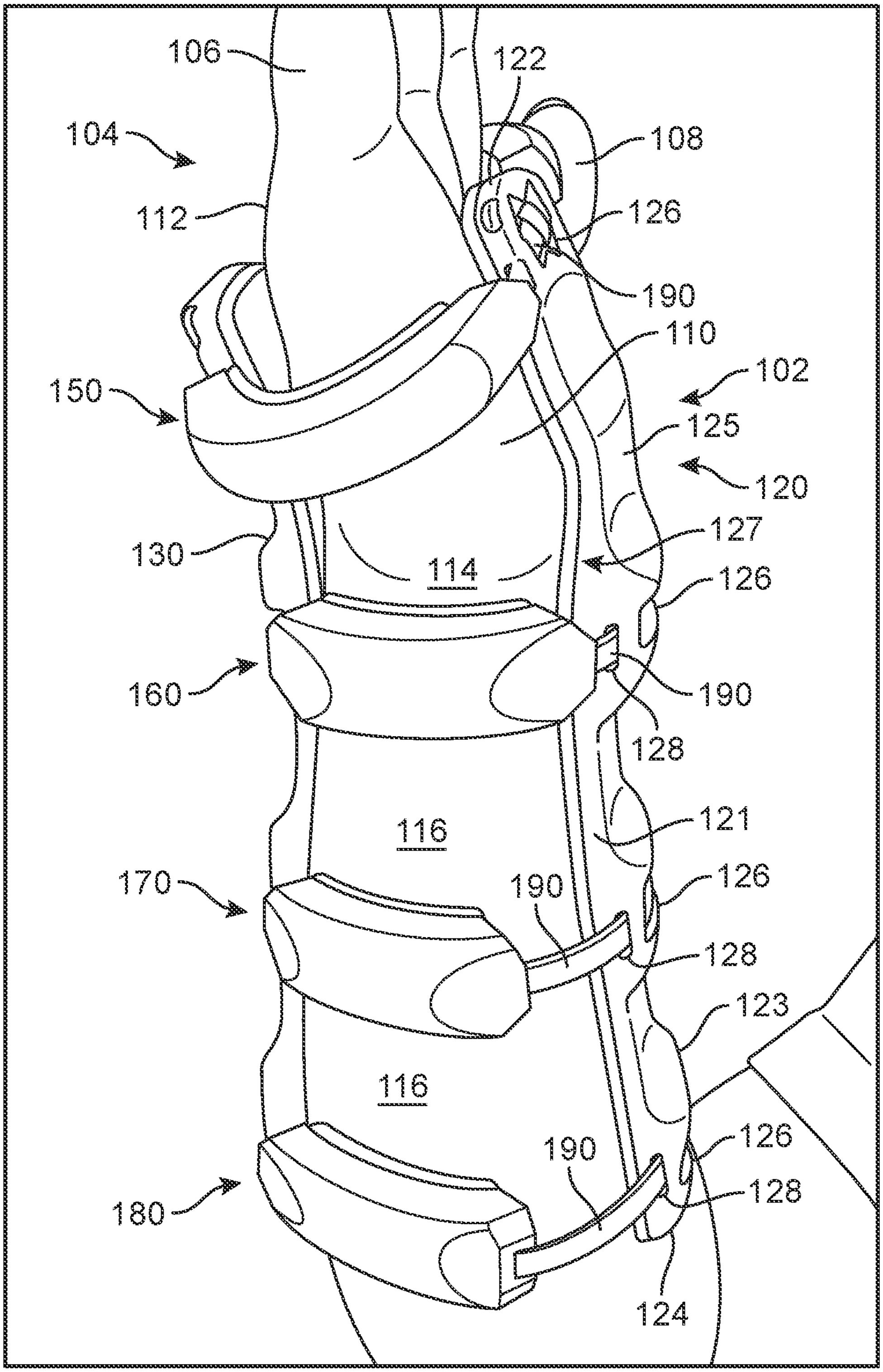
FIG. 1 is a side view of an assembled splint in accordance with this disclosure, on a wearer's right hand.

FIG. 1 shows an embodiment of a splint 102 in accordance with this disclosure. Splint 102 may be worn on a wearer's limb 104. In this embodiment, limb 104 may be a human arm and hand. Specifically, limb 104 may include a wearer's fingers 106, a wearer's thumb 108, a wearer's hand 110, a wearer's back of hand 112, a wearer's wrist 114, and a wearer's forearm 116.

Splint 102 may fit snugly around limb 104 in order to immobilize the limb, so as to promote healing from a sprain or bone break. In order to securely immobilize limb 104, splint 102 may include a front spine 120 and a back spine 130. Front spine 120 and back spine 130 may be aligned lengthwise along limb 104 on opposite sides of the limb 104.

Specifically, front spine 120 may include a top end 122 that is adjacent to hand 110 and bottom end 124 that is adjacent to forearm 116. Front spine 120 may include medial side 121 that is opposite lateral side 123, and outer surface 125 that is opposite inner surface 127. On outer surface 125 may be located several attachment structures 126. Each attachment structure 126 may include a side hole 128 that receives a cable tie 190.

Each of a plurality of cable ties 190 may then extend through a set of beads 150, 160, 170, 180. Each set of beads is designed to conform to the wearer's appendage by surrounding the limb 104 on opposite sides of the limb 104. Specifically, set of palm beads 150 may be configured to fit on opposite sides of the wearer's hand and hand 110; set of wrist beads 160 may be configured to fit on opposite sides of the wearer's wrist 114; first set of forearm beads 170 may be configured to fit on opposite sides of the wearer's forearm 116; and second set of forearm beads 180 may also be configured to fit on opposite sides of the wearer's forearm 116. The beads 150, 160, 170, 180 may further immobilize the limb 104 to promote healing, and may also protect limb 104 against impact. Beads 150, 160, 170, 180 may also protect limb 104 by allowing appropriate (but not undue) compression between front spine 120 and back spine 130.

Back spine 130 may be configured to extend along a back side of a wearer's limb 104, specifically the wearer's forearm 116 and hand 110. The plurality of cable ties 190 may extend through a through-hole in each bead in each set of beads 150, 160, 170, 170, 180 and connect the front spine 120 to the back spine 130. In this way, front spine 120 and back spine 130 may "sandwich" limb 104 between them, so as to immobilize the limb 104.

Figure 2:
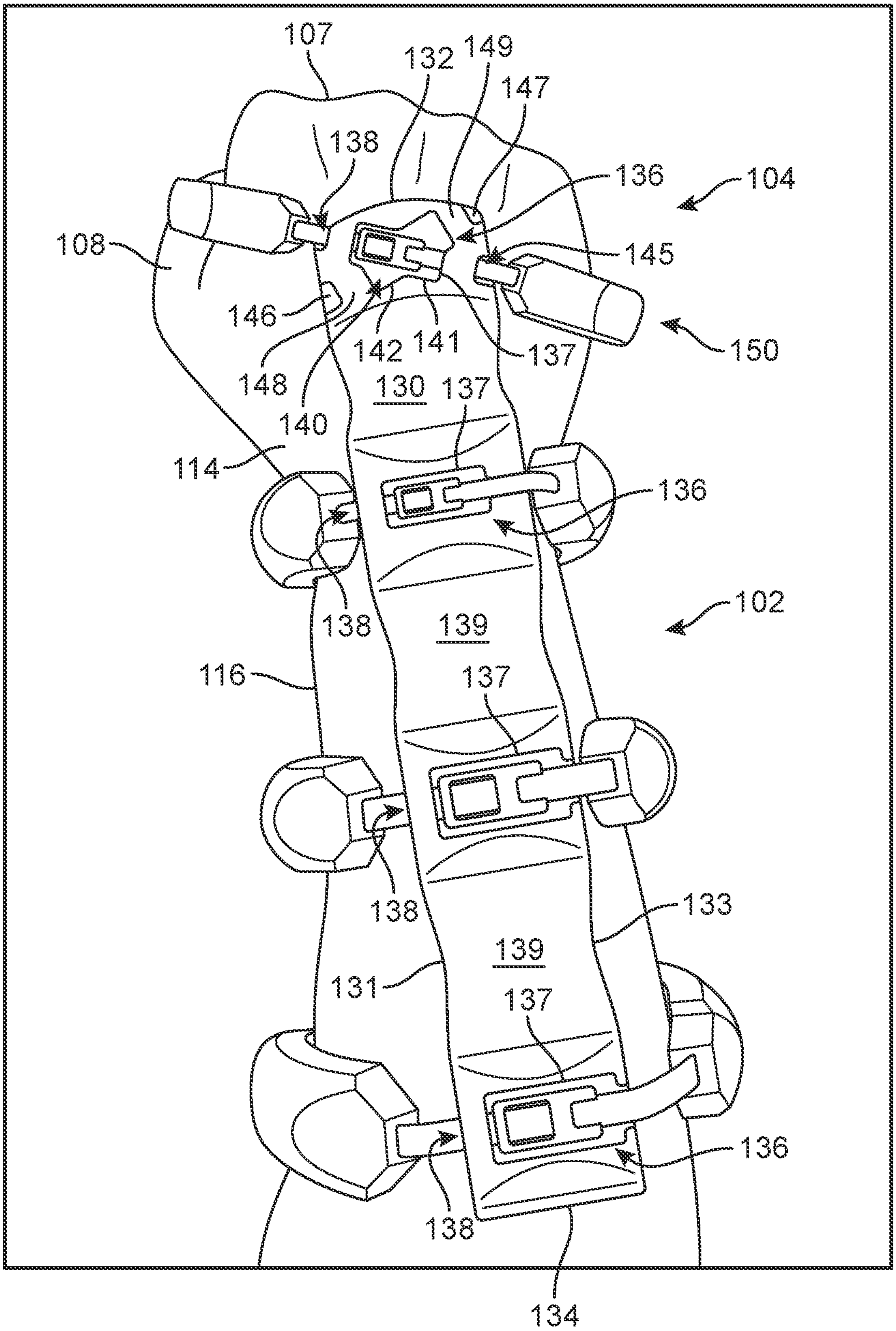
FIG. 2 is a top view of an assembled splint in accordance with this disclosure, on a wearer's right hand.

FIG. 2 shows a top view of splint 102. In particular, FIG. 2 shows back spine 130 in further detail. Back spine 130 may include medial side 131 that is opposite lateral side 133. Back spine 130 may also include top end 132, adjacent to wearer's hand 110 and knuckles 107, that is opposite bottom end 134 adjacent to wearer's forearm 116.

Back spine 130 may include a plurality of attachment structures 136 on the outer surface 139. Each attachment structure 136 may include a recessed area 137 design to accommodate a portion of each of the plurality of cable ties 190. Also included in each attachment structure 136 may be a side hole 138 designed to allow each cable tie 190 to go there through. In this way, cable ties 190 may secure back spine 130 to front spine 120 at the attachment areas 126, 136 on each. The two spines 120, 130 may therefore immobilize the wearer's limb 104, while the limb is also protected by beads 150, 160, 170, 180.

Back spine 130 may also include a first attachment structure 140 that allows for the spines 120, 130 to be used in multiple orientations. Specifically, first attachment structure 140 includes recessed area 141 that allows a cable tie 190 to be in a first orientation. Recessed area 141 that allows first orientation may correspond to a right hand limb 104, as shown in FIG. 2. First attachment structure 140 may also include second recessed area 142 that allows a cable tie 190 to be inserted into first attachment structure in a second orientation, which may correspond to a left hand limb 104 (not shown). First recessed area 141 may include first through-hole 138 and second through-hole 145, that allow cable tie 190 to extend there through. Second recessed area 142 may include third through-hole 146 and fourth through-hole 147, that allow cable tie 190 to extend there through.

Front spine 120 may also have corresponding recessed areas that allow for multiple orientations of a cable tie, as is shown in FIG. 1. In this way, set of palm beads 150 may be oriented so that they fit a right hand (as shown) or a left hand. As a result, the same splint may be used for either a right hand or a left hand without the need for additional parts by changing the orientation of a cable tie that go through the spines.

Figure 3:
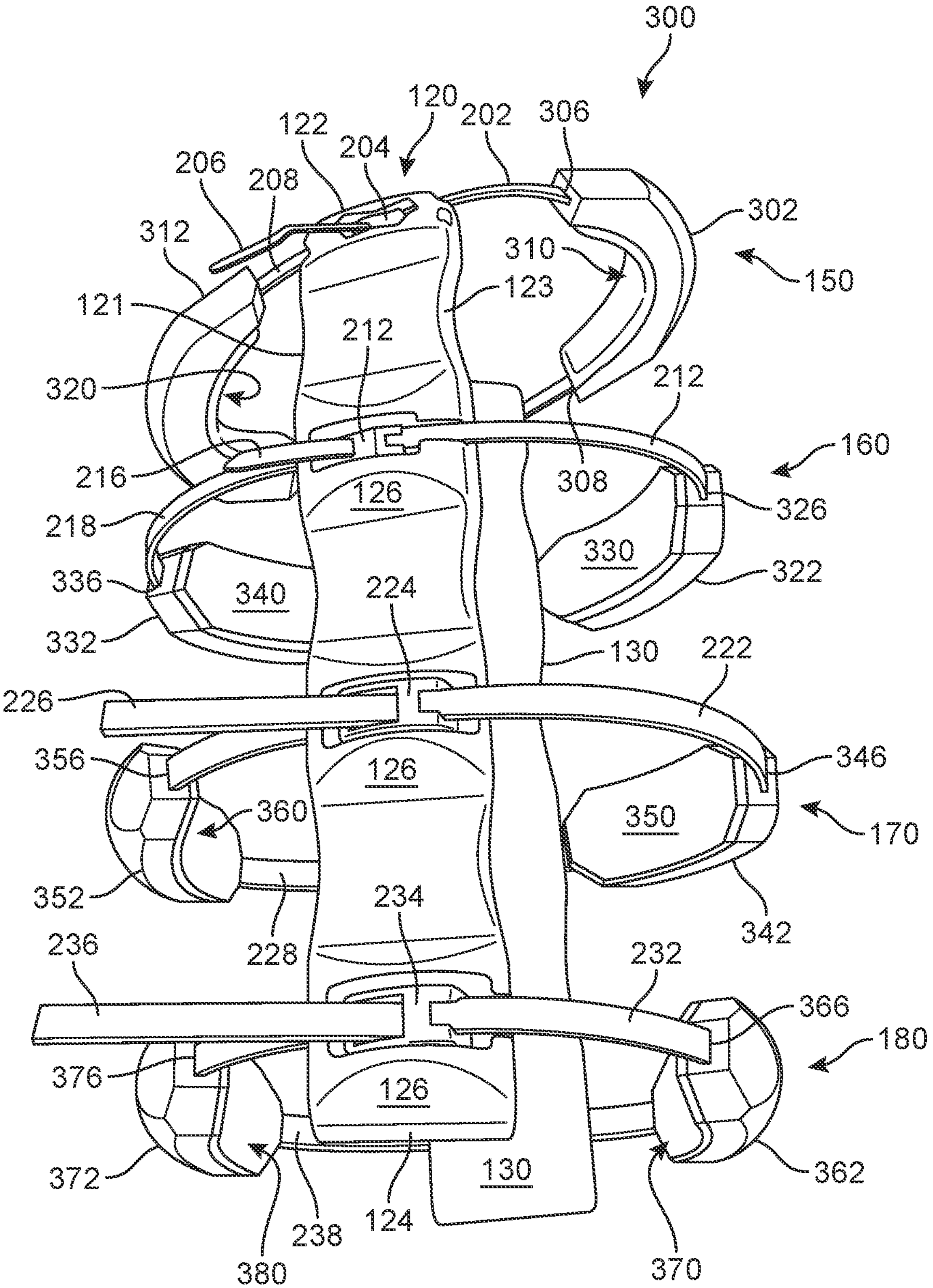
FIG. 3 is a front view of an assembled splint in accordance with this disclosure.

FIG. 3 shows a splint 300 before it is worn by any wearer. Splint 300 is shown from a top view of front spine 120, this view can be understood as having been rotated roughly 180 degrees from the view of FIG. 2. In particular, FIG. 3 shows in further detail how the cable ties attach the beads to the spines, and the spines to each other.

In particular splint 300 may include first cable tie 202. Cable tie 202 may extend through first palm bead 302, through through-hole 306 therein, and one end may extend through ratchet head 204 of second cable tie 208, so that excess length 206 sticks out of ratchet head 204. Second cable tie 208 may similarly extend from attachment structure 126, through second palm bead 312, and down into an attachment structure (not shown) in back spine 130. In this way, the two cable ties 202 and 208 together encircle a wearer's limb, and tie together the beads 302, 312 with the spines 120, 130. As shown in FIG. 3, the cable ties have not yet been fully tightened around a limb—but instead merely have a short excess length 206 that can be pulled upon to further tighten the cable tie around a limb. After fitting to a limb, excess length 206 may be removed by cutting the cable tie 202 just past where it exits ratchet head 204.

In the same way, third cable tie 212 may extend through first wrist bead 322 through through-hole 326 therein. Third cable tie 212 may then attach to back spine 130 at an attachment structure (not shown) at one end, and at ratchet head 212 of fourth cable tie 218 at the other end. Fourth cable tie 218 may extend through second wrist bead 332 at through-hole 336, and extend into a ratchet head (not shown) of third cable tie 212 on back spine 130. Excess length 216 of third cable tie 212 may then be pulled by user or wearer to tighten wrist beads 322, 332 around the wearer's wrist.

The same mechanism of action also applies to upper forearm beads 170 and lower forearm beads 180. Namely, fifth cable tie 222 may extend through first upper forearm bead 342 and around down to back spine 130—while also extending through ratchet head 224 of sixth cable tie 228 at the other end. Sixth cable tie 228 may extend from ratchet head 224 in attachment structure 126, through second upper forearm bead 352 through through-hole 356 therein, and down into ratchet head (not shown) of fifth cable tie 222 at back spine 130. Similarly, seventh cable tie 232 may extend from ratchet head 234 in attachment structure 126 on front spine 120 through first lower forearm bead 363 through through-hole 366 and around down into an attachment structure (not shown) on back spine 130. Eighth cable tie 238 may start at ratchet head 234 recessed into attachment structure 126, around through second lower forearm bead 372 through through-hole 376 and extend through a ratchet head (not shown) that is part of seventh cable tie 232 in an attachment structure on back spine 130. Excess length 226 of fifth cable tie 222, and excess length 236 of seventh cable tie 232, may then be pulled to tighten that respective cable tie. As a result, each bead in each set of beads may be independently tightened around the limb by pulling one of the two cable ties joining that loop.

FIG. 3 also shows how each respective bead may include a foam layer on an inner surface thereof. A foam layer may act as cushion when the bead presses against a wearer's skin, while the rigidity of the bead itself may nonetheless still immobilize the limb. Generally, a foam layer may be waterproof so that the splint may be exposed to water and other elements. A variety of known closed-cell foams are known in the art to be waterproof. In some embodiments, a foam layer may be a polyethylene foam. In a particular embodiment, a foam layer on a bead may be a one-eighth inch thick adhesive backed closed cell Plastazote® foam.

Specifically, FIG. 3 shows how first palm bead 302 may have foam layer 310 on an inner surface thereof. Second palm bead 312 may include foam layer 320. First wrist bead 322 may include foam layer 330. Second wrist bead 332 may include foam layer 340 thereof. First upper forearm bead 342 may include foam layer 350. Second upper forearm bead 352 may include foam layer 360. First lower forearm bead 362 may include foam layer 370. Finally, second lower forearm bead 372 may include foam layer 380.

Additionally, in other embodiments similar to the splint of FIG. 3 but not shown, each of the beads 302, 312, 322, 332 etc. may include rubber stoppers on either end of each through-hole 306, 326, 336 etc. These rubber stoppers may secure each bead in place relative to the respective cable tie, so the beads do not slide back and forth along the cable ties. Thus, each bead may include two rubber stoppers—one at each end where the cable tie extends through the through-hole.

Figure 4:
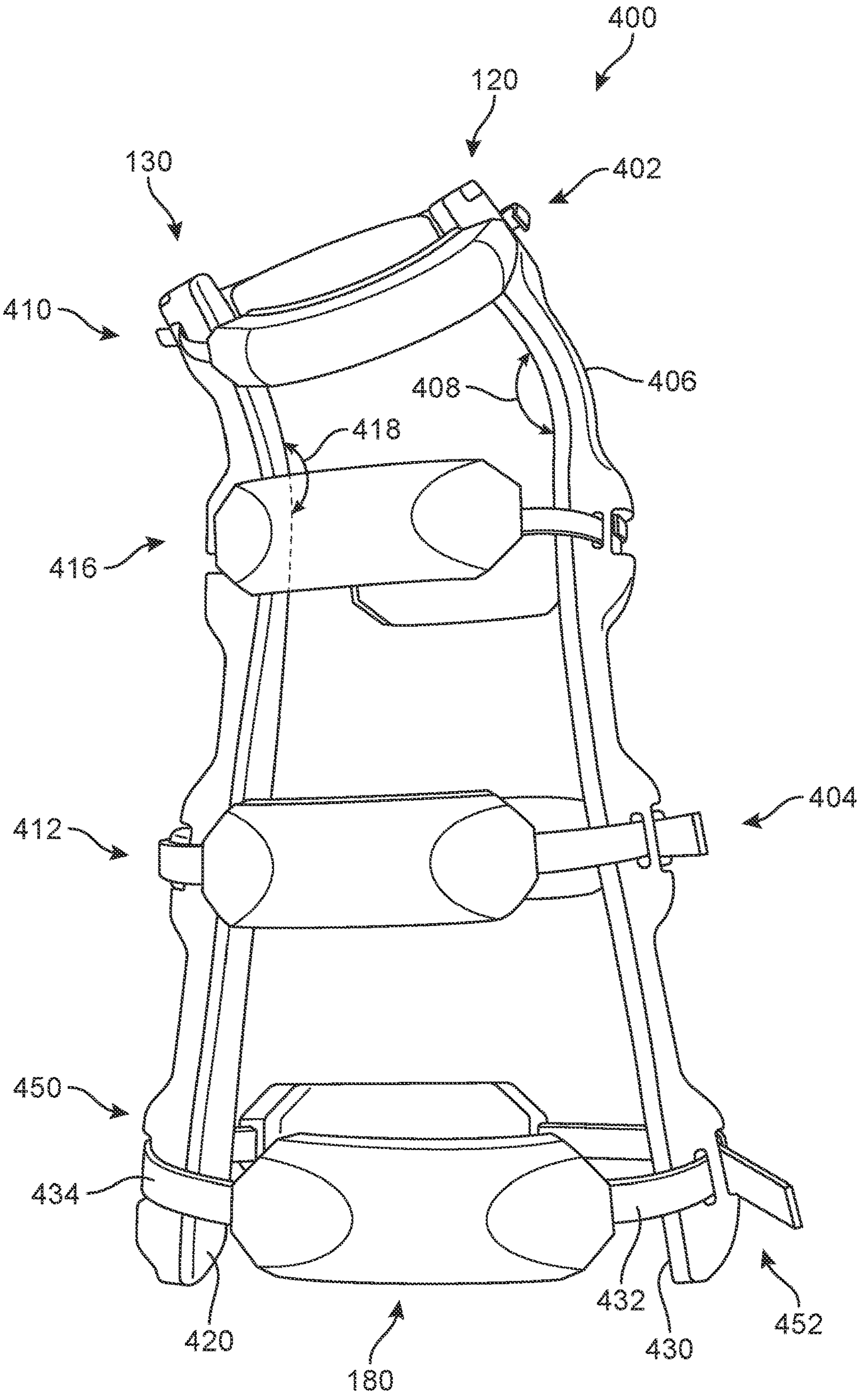
FIG. 4 is a medial (pinky) side view of an assembled splint in accordance with this disclosure.

Next, FIG. 4 shows a side view of a splint 400 before it is placed on a wearer's limb. In this view, the angled shape of the two spines is further illustrated. Namely, front spine 120 includes bend 406. Bend 406 may be located between a front spine upper portion 402 and a front spine lower portion 404. Upper portion 402 may correspond to a wearer's hand, while lower portion may correspond to a wearer's wrist and forearm. Bend 406 may be of angle 408. Angle 408 may be about 15 degrees at an vertical angle relative to the wearer's forearm.

Similarly in FIG. 4, back spine 130 may include bend 416 therein. Bend 416 may be located between back spine upper portion 410 and back spine lower portion 412. Bend 416 may also be approximate 15 degrees at an vertical angle relative to the wearer's forearm. This angle may immobilize the wearer's wrist at a comfortable angle for long durations of wear, such as the many weeks or months necessary for a bone break to heal.

Importantly, the angle of bend 406 and bend 416 may be customized in order to better fit a wearer's limb. While front spine 120 and back spine 130 may be manufactured with bends 406, 416 as shown, the shape of front spine 120 and back spine 130 may also nonetheless be customized by applying heat. In such embodiments, the spines 120, 130 may be comprised of a thermoplastic polymer. In some embodiments, the spines may consist essentially of a thermoplastic polymer.

Thermoplastic polymers, as is known in the art, include any polymer material that becomes pliable or moldable at a certain elevated temperature and solidifies upon cooling. A wide range of known thermoplastic polymers may be used to form the spines. In particular embodiments, the spines may be formed from polylactide aka "PLA" or "polylactic acid". In some embodiments, the spines may consist essentially of PLA polymer.

In various embodiments, depending on which specific thermoplastic polymer is used for the spines, the spines may be heated through various methods. For example, the spines may be heated with a heat gun, or in an oven at 220 degrees for 2-3 minutes, or in boiling water for approximately 90 seconds. Subsequently, the spines may be changed in shape. For example, bend 406 may be independently increased or decreased in angle 408, bend 416 may be independently increased or decreased in angle 418—or both bends 406, 416 may be decreased or increased by matching degrees. This may therefore allow the splint to be further customized in shape to better fit a wearer's limb.

FIG. 4 also illustrates and embodiment where the spines include a foam layer thereon. Namely, front spine 120 may include foam layer 430 on an inner surface thereof. Namely, foam layer 430 may be disposed on an opposite side as attachment structures 126 which are variously illustrated and discussed above. Back spine 130 may similarly include foam layer 420 on an inner surface thereof. As was discussed above with respect to foam layers on the beads, foam layers on the spines may also increase comfort against a wearer's skin. Foam layers 420, 430 may be of the same type and thickness of foam as discussed above with respect to foam layers 310, 320 etc.

Figure 5:
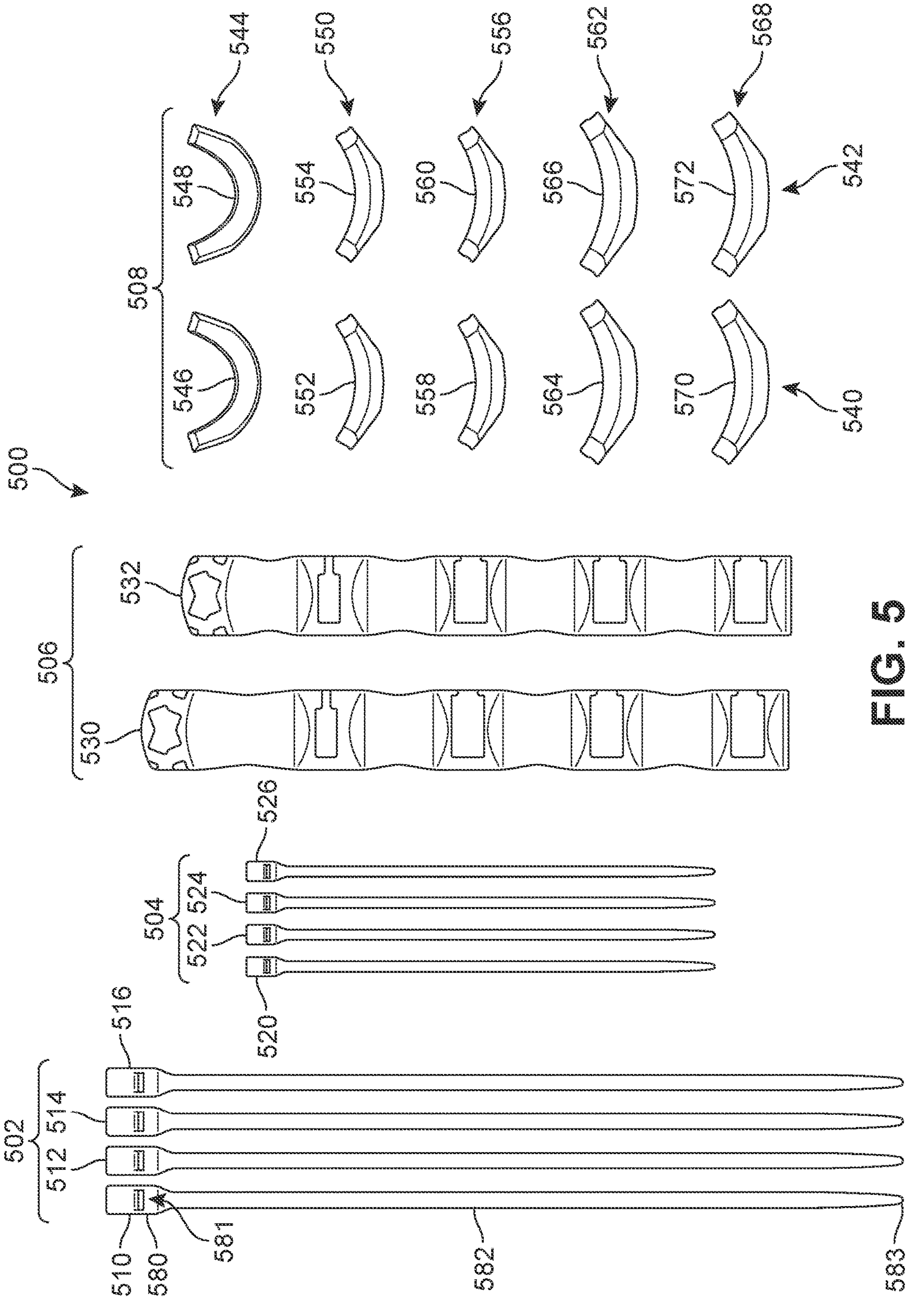
FIG. 5 is a top view of the various components of a splint kit in accordance with this disclosure.

FIG. 5 shows a kit 500 in accordance with this disclosure, before it is assembled into a splint. Kit 500 may include a plurality of large cable ties 502, a plurality of small cable ties 504, two spines 506, and a plurality of sets of beads 508.

Plurality of large cable ties 502 may include first large cable tie 510, second large cable tie 512, third large cable tie 514, and fourth large cable tie 516. Large cable ties 502 may be used to provide a larger fit around a larger diameter limb. Alternatively, in some embodiments, large cable ties 502 may be used to surround an entire limb by extending through both beads in a set of beads and looping back on itself—instead of using two cable ties per set of beads as discussed above.

Each cable tie includes a head 580 that includes a ratchet mechanism 581. As is generally known, cable ties broadly include a flexible tape section 582 with teeth that engage with a pawl in the head 580 to form a ratchet 581 so that as the free end of the tape section 583 is pulled the cable tie tightens and does not come undone. Nylon cable ties therefore may act as an tight closure mechanism, that cannot come undone unless the cable tie is cut or a release mechanism (not shown) on certain types of cable ties is activated. Accordingly, the cable ties achieve a ratcheting system that locks the beads and spines in place relative to each other around the wearer's limb.

The cable ties may be low profile cable ties, whereby the head 510 has a minimal thickness—so that head 510 may fit into recessed area 137 in the attachment structures on the spines.

Next, in the embodiment of a kit 500 shown in FIG. 5, each of the two spine 530 and 532 in the set of spines 506 may include five attachment areas as shown. This embodiment may differ from the embodiments shown in FIGS. 1-4 which have four attachment areas. Spines 506 with five attachment areas may be relatively longer than spines with only four attachment areas, and so may be configured to fit larger limbs or larger wearer's etc.

In the same way, kit 500 may include five sets of beads within plurality 508 of sets of beads. Namely, first set of beads 544 may include first bead 546 and second bead 548. Beads 546 and 548 may be palm beads, configured to fit around the hand of a wearer. Second set of beads 550 may include first bead 552 and second bead 554, which may be configured to fit around a wearer's wrist. Third set of beads 556 may include first bead 558 and second bead 560, which may be configured to fit around a wearer's upper forearm. Fourth set of beads 562 may include first bead 564 and second bead 566, which may be configured to fit around a wearer's mid-forearm. Finally, fifth set of beads 568 may include first bead 570 and second bead 572, which may be configured to fit around a wearer's lower forearm. The plurality of sets of beads 508 may also be considered to include a lateral subset of beads 540 and a medial subset of beads 542.

Accordingly, kit 500 may be assembled into a splint in accordance with this disclosure. In some embodiments, the components of kit 500 may be assembled by the wearer themselves, without intervention by a medical professional.

Figure 6:
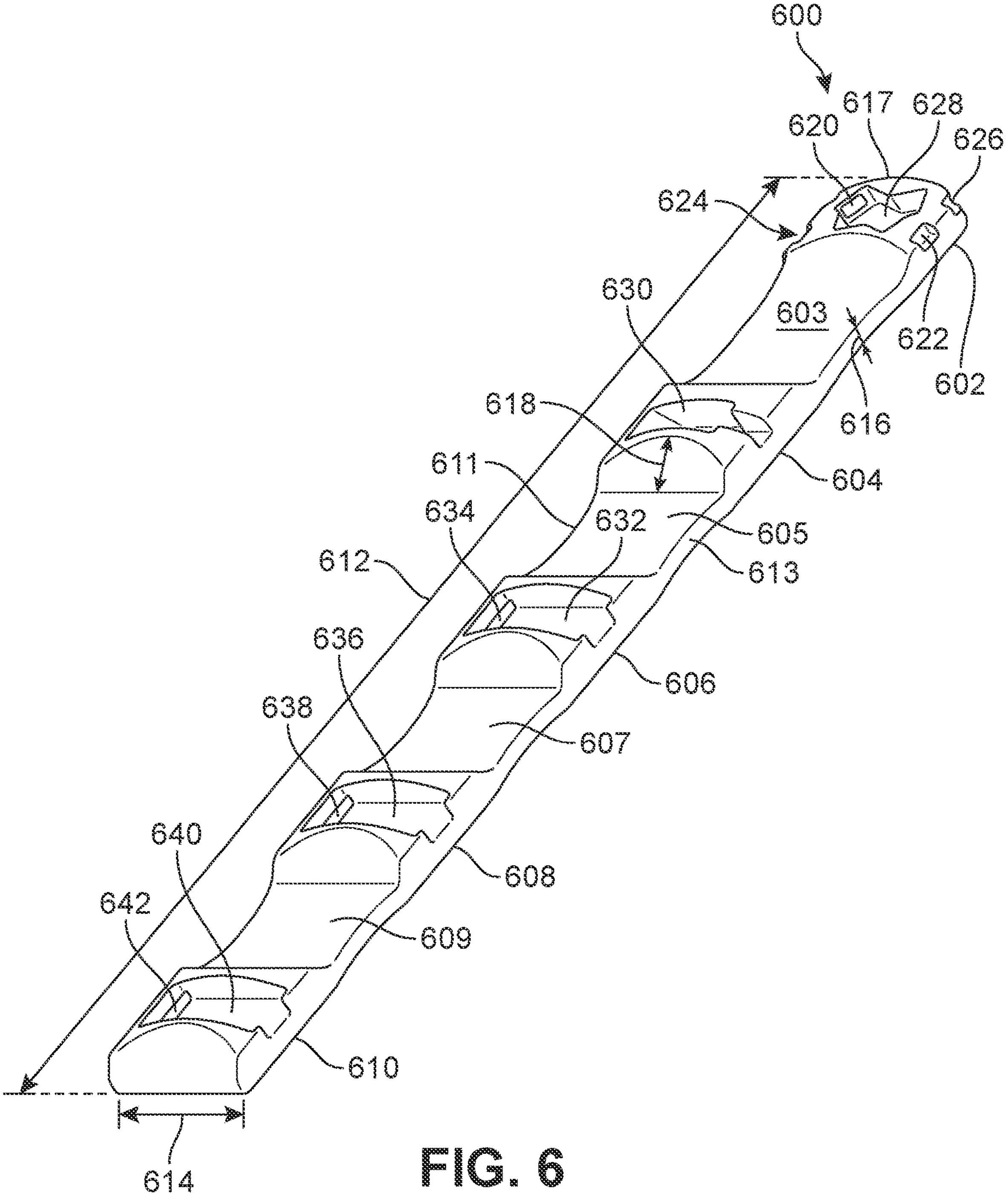
FIG. 6 is an isometric view of the large long palm spine component of a splint kit in accordance with this disclosure.

FIG. 6 shows an embodiment of a first spine 600. First spine 600 may have length 612, width 614, and thickness 616. Generally, each of length 612, width 614, and thickness 616 may be configured to fit along the length of a wearer's limb. In various embodiments, the limb may be an arm, a wrist, an elbow, a finger, a thumb, a leg, a knee, an ankle, or a foot. First spine 600 is also shown as flat, without any curvature—however it may subsequently include a bend upon remolding with heat as discussed above. Additionally, length 612 may be customized by trimming or cutting off a portion of first spine.

First spine 600 may include first attachment structure 602 that includes recessed area 628. In order to allow spine 600 to be used in either a right hand configuration or a left hand configuration, first attachment structure 602 may include first side hole 620 opposite second side hole 622—and also third side hole 624 that is opposite fourth side hole 626. As discussed above, a cable tie may be threaded through first side hole 620 and second side hole 622, or through third side hole 624 and fourth side hole 626.

Adjacent to first attachment structure 602 may be first flat area 603 on the outer surface of the spine 600. Next, spine 600 may include second attachment structure 604, third attachment structure 606, fourth attachment structure 608, and fifth attachment structure 610. Between each attachment structure may be adjacent to a respective flat area 605, 607, 609. Each attachment structure respectively includes a recessed area 630, 632, 636, 640 with an opening for a cable tie head. Each attachment structure also respectively includes a side hole 634, 638, 642 through which a cable tie end can be threaded. Each attachment structure may have a height 618, which may be tall enough to fit a low profile cable tie head and no taller.

Figure 7:
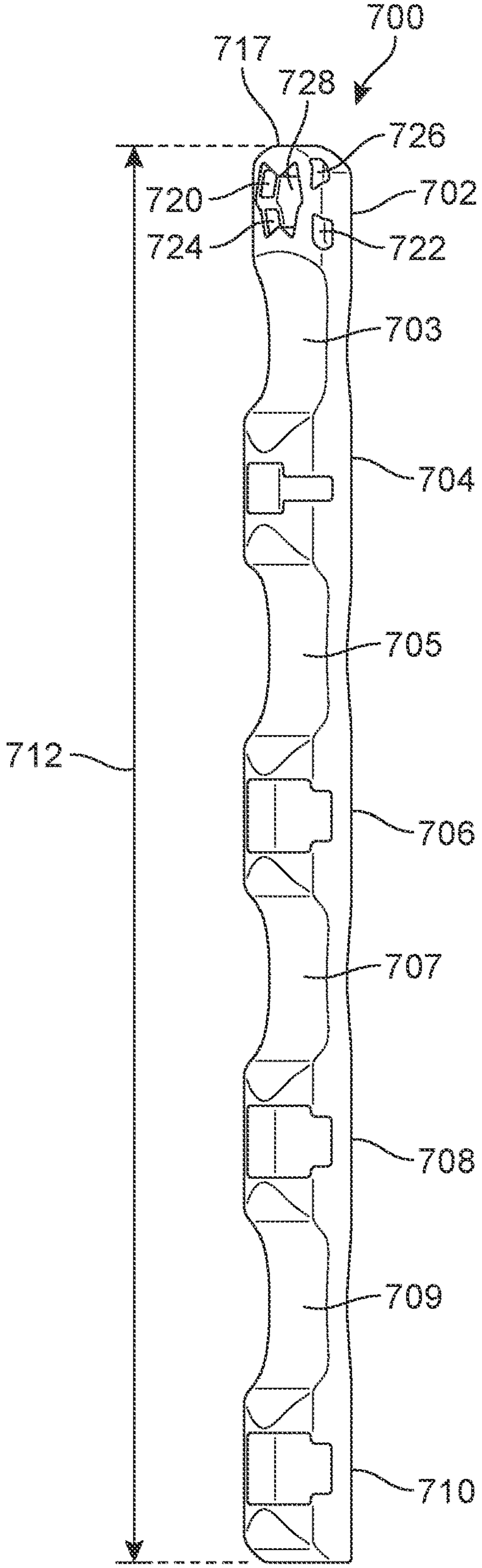
FIG. 7 is an side isometric view of the large long back spine component of a splint kit in accordance with this disclosure.

FIG. 7 shows a side isometric view of a second spine 700. Second spine 700 may have length 712, which may be less than length 612 of first spine 600 as is shown in FIG. 5. Length 712 may be configured to correspond to a wearer's forearm and top of hand, in order to lay on top of a wearer's hand below the knuckles.

Similar to as discussed above with respect to first spine 600 in FIG. 6, second spine 700 shown in FIG. 7 may have a first attachment structure 702. First attachment structure 702 may include a recessed area 728 that is contiguous with first side hole 720, second side hole 722, third side hole 724, and fourth side hole 726. As discussed above, the four side holes allow a cable tie to be positioned through first attachment structure 702 in either of two configurations—in order to allow a first set of beads to be placed in e.g. a right hand configuration or a left hand configuration.

Second spine 700 next includes flat area 703, second attachment structure 704, second flat area 705, third attachment structure 706, third flat area 707, fourth attachment structure 708, fourth flat area 709, and fifth attachment structure 710. Each of the attachment structures 702, 704, 706, 708, 710 may correspond to a respective attachment structure 602, 604, 606, 608, 610 on first spine 600.

Figure 8:
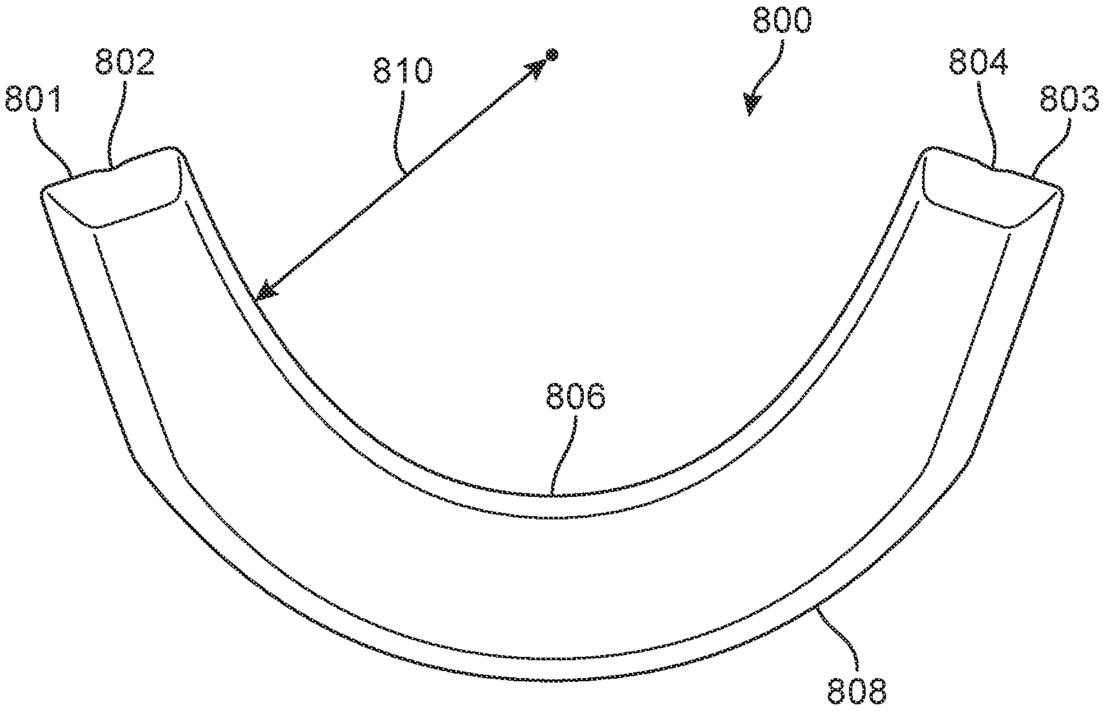
FIG. 8 is a side view of the large palm bead component of a splint kit in accordance with this disclosure.
Figure 9:
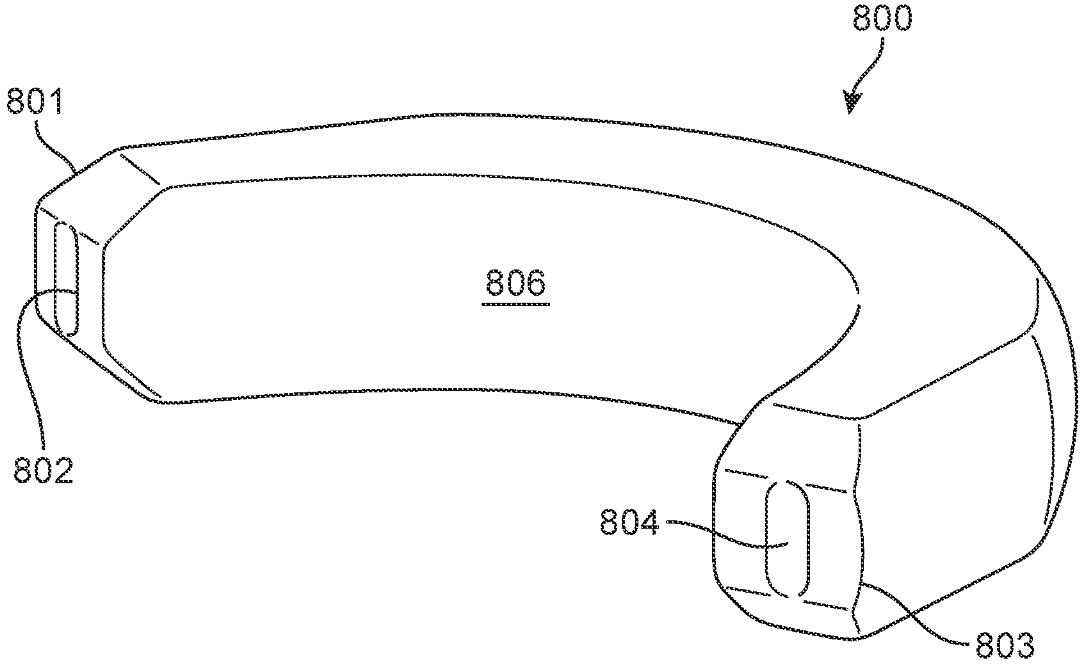
FIG. 9 is an isometric view of the large palm bead component of a splint kit in accordance with this disclosure.

FIGS. 8 and 9 show an embodiment of a first bead 800. First bead 800 may have first end 801, second end 803, inner surface 806, and outer surface 808. First end 801 include first end of through-hole 802, while second end 803 may include a corresponding second end of through-hole 804. In this way, the through-hole extends through the center of first bead 800 along its central axis.

First bead 800 is also curved in a roughly horseshoe shape, with each end 801, 803 curved upward and relatively towards each other. This curvature may be described by radius of curvature 810. In some embodiments, first bead 800 may be a palm bead configured to fit into the webbing between a wearer's thumb and fingers or around the side of the wearer's hand. First bead 800 may correspond to first bead 546 in set of beads 544 shown in kit 500 of FIG. 5. Bead 548 may have similar dimensions and radius of curvature as bead 800, such that set of beads 544 may surround a wearer's hand on either side.

Figure 10:
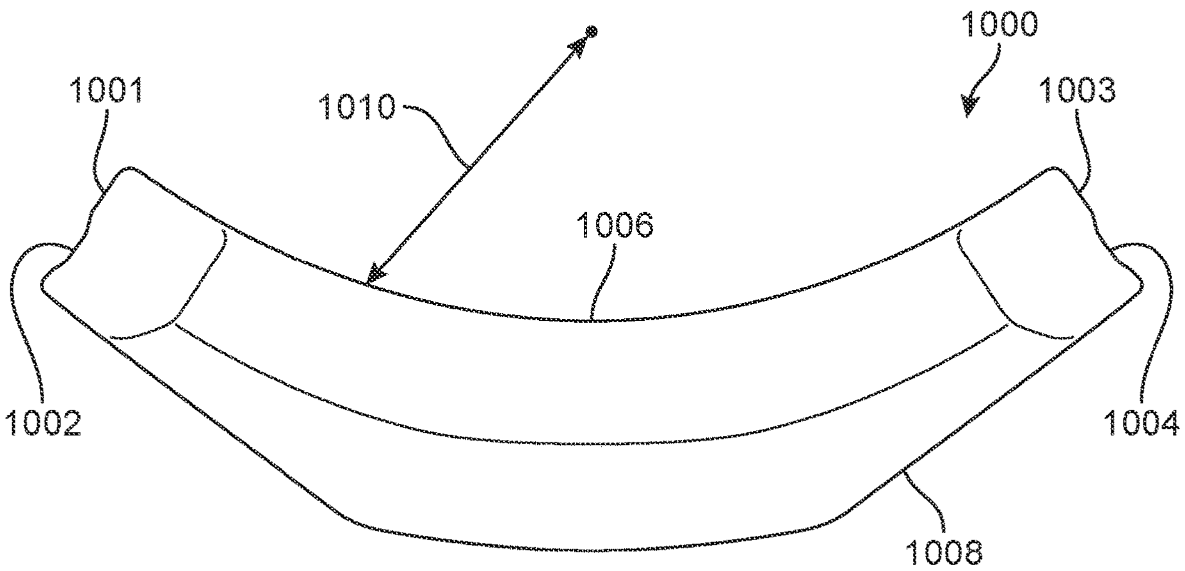
FIG. 10 is a side view of the large wrist bead component of a splint kit in accordance with this disclosure.
Figure 11:
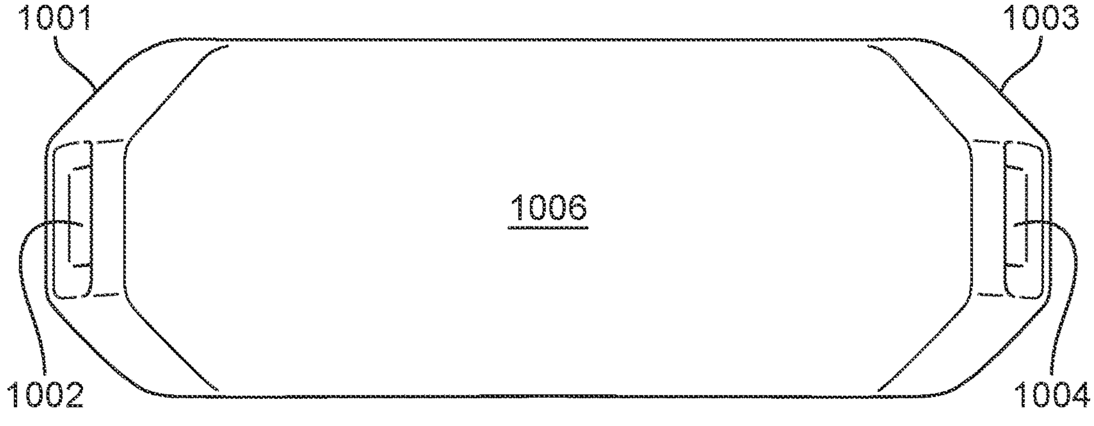
FIG. 11 is a back view of the inner surface of the large wrist bead component of a splint kit in accordance with this disclosure.

FIGS. 10 and 11 show an embodiment of a second bead 1000. Second bead 1000 may have first end 1001, second end 1003, inner surface 1006, and outer surface 1008. First end 1001 may include first end of through-hole 1002, while second end 1003 may include second end of through-hole 1004. Second bead 1000 may also be curved upward in a horseshoe like shape, with radius of curvature 1010. In some embodiments, radius of curvature 1010 may be greater than radius of curvature 810—that is, second bead 1000 may have less curvature than first bead 800. Second bead 1000 and it's radius of curvature 1010 may be configured to fit a wearer's wrist. Second bead 1000 may correspond to bead 552 in set of beads 550 in kit 500 of FIG. 5

Figure 12:
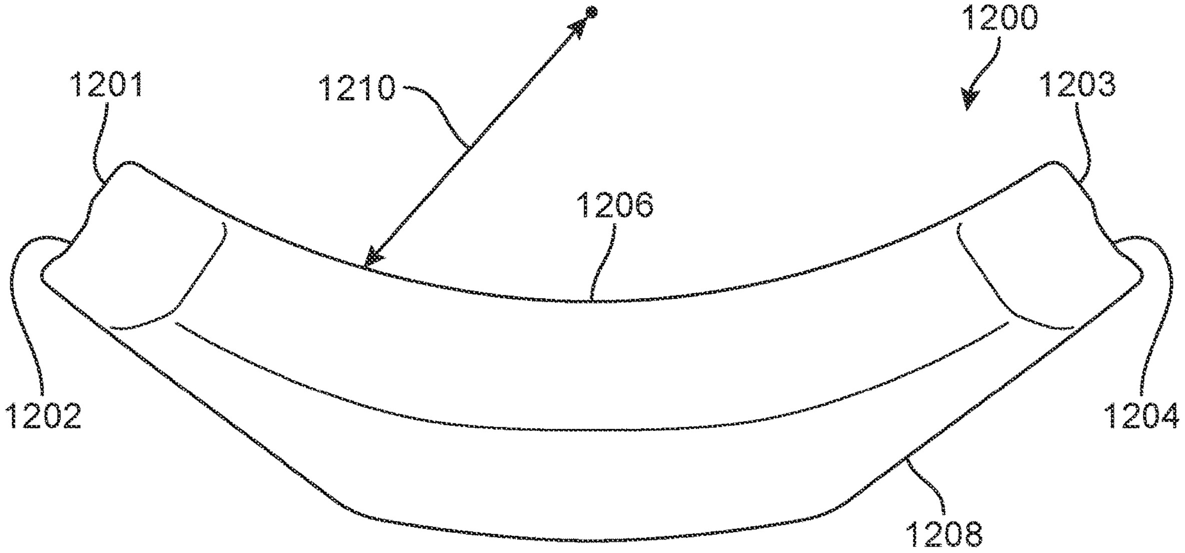
FIG. 12 is a side view of the large forearm-wrist bead component of a splint kit in accordance with this disclosure.
Figure 13:
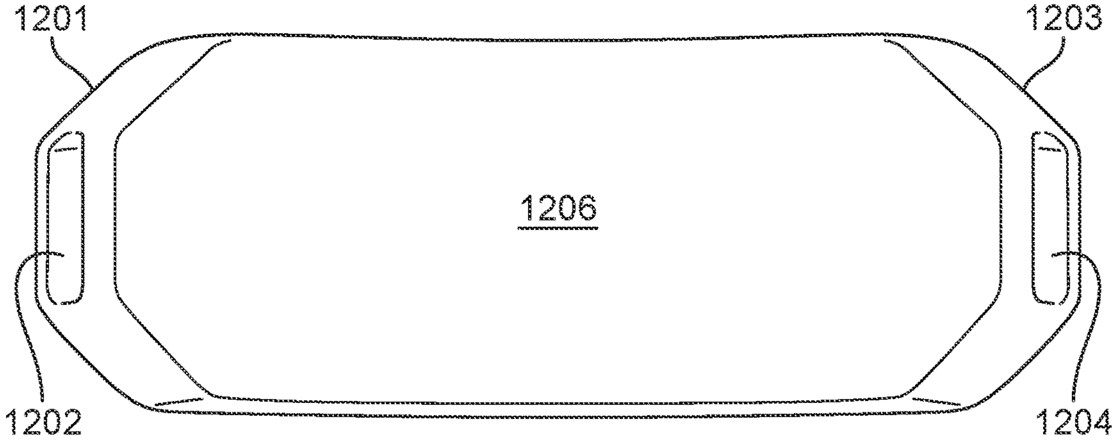
FIG. 13 is a back view of the inner surface of the large forearm-wrist bead component of a splint kit in accordance with this disclosure.

FIGS. 12 and 13 show an embodiment of a third bead 1200. Third bead 1200 may have first end 1201, second end 1203, inner surface 1206, and outer surface 1208. First end 1201 may include first end of through-hole 1202, while second end 1203 may include second end of through-hole 1204. Third bead 1200 may have radius of curvature 1210, which may be larger than radius of curvature 1010 and radius of curvature 810. That is, third bead 1200 may be less curved upward than second bead 1000 or first bead 800. Third bead 1200 may be configured in shape and radius of curvature 1210 to a wearer's upper forearm. Third bead 1200 may also correspond to bead 558 in set of beads 556 in kit 500.

Figure 14:
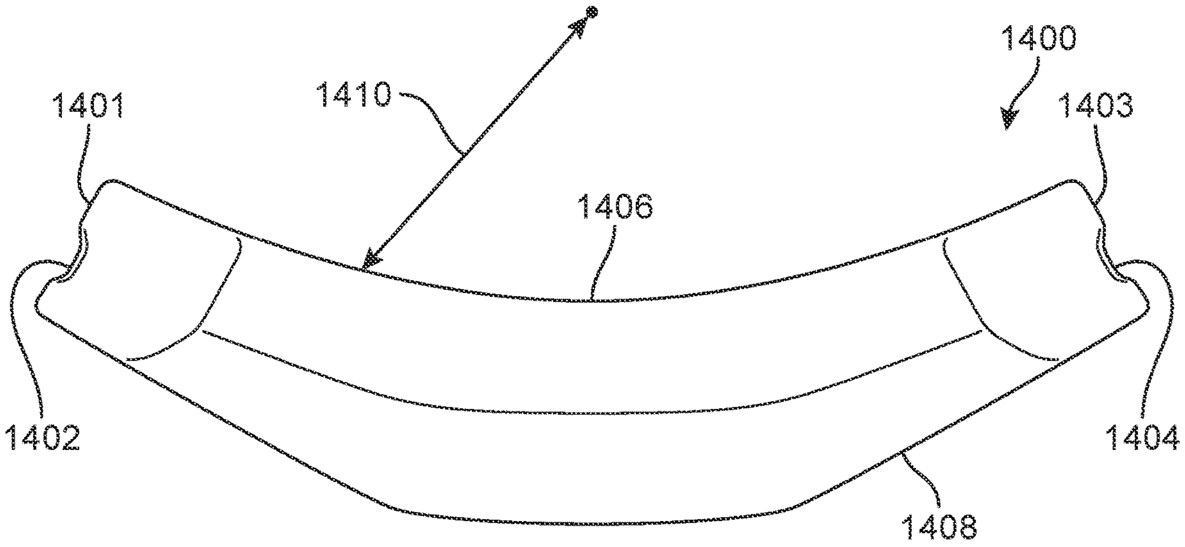
FIG. 14 is a side view of the large forearm bead component of a splint kit in accordance with this disclosure.
Figure 15:
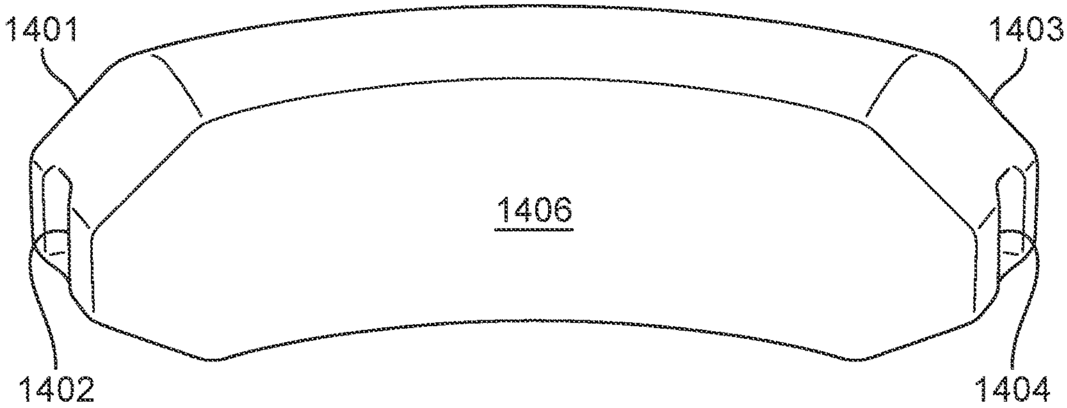
FIG. 15 is a top isometric view of the large forearm bead component of a splint kit in accordance with this disclosure.

Finally, FIGS. 14 and 15 show an embodiment of a fourth bead 1400. Fourth bead 1400 may have first end 1401, second end 1403, inner surface 1406, and outer surface 1408. First end 1401 may include first end of through-hole 1402, while second end 1403 may include second end of through-hole 1404. Fourth bead 1400 may have radius of curvature 1410—which may be larger than radius of curvature 1210, larger than radius of curvature 1010, and larger than radius of curvature 810. That is, fourth bead 1400 may be less curved upward than any of first bead 800, second bead 1000, or third bead 1200. Fourth bead may be configured in shape and radius of curvature 1410 to a wearer's forearm. Fourth bead 1400 may correspond to any of beads 564, 566, 570, or 572 in kit 500 shown in FIG. 5.

Thus, the plurality of sets of beads 508 may include sets of beads 544, 550, 556, and 562/568 that each have different radiuses of curvature in order to best fit against different portions of a wearer's limb. In this way, a wearer's limb may be snugly immobilized by the spines and beads in order to promote healing of an injury.

Each of the beads discussed above may be made of a thermoplastic or thermoset polymer. In one embodiment, the beads may be made of ABS polymer. In some embodiments, the beads may consist essentially of ABS polymer.

Each of the spines and each of the beads discussed above may be made by any of various known polymer manufacturing techniques. In some embodiments, any of the spines and the beads may be manufactured by 3D printing with a polymer material. In other embodiments, the spines and beads may be injection molded. In embodiments where the components may be injection molded, some aspects of the components may differ from as shown and discussed herein. For example, injection molded components of a splint in accordance with this disclosure may be hollow in one or more areas. Nonetheless, the overall shape and function of any such injection molded would stay the same in order to achieve the function of immobilizing a wearer's limb.

Accordingly, the various components discussed above may be assembled together to form a customizable sized waterproof splint. The components may be assembled by a medical professional, or by an end user without intervention from a medical professional.

While various embodiments of the disclosure have been described, the description is intended to be exemplary, rather than limiting and it will be apparent to those of ordinary skill in the art that many more embodiments and implementations are possible that are within the scope of the disclosure. Accordingly, the disclosure is not to be restricted except in light of the attached claims and their equivalents. Also, various modifications and changes may be made within the scope of the attached claims.

I claim:

1. A kit for assembling a waterproof wrist splint, comprising:

a back spine, configured to extend along a back side of a wearer's forearm and hand;

a front spine, configured to extend along a front side of the wearer's forearm and hand;

each of the back spine and the front spine respectively including a plurality of attachment structures therein on an outer surface thereof;

a pair of palm beads, configured to fit on opposite sides of the wearer's hand;

a pair of wrist beads, configured to fit on opposite sides of the wearer's wrist;

at least one pair of forearm beads, each of the pair of forearm beads configured to fit on opposite sides of the wearer's forearm;

each of the palm beads, wrist beads, and forearm beads including a through-hole extending from a first side to a second side thereof; and a plurality of cable ties, each of the plurality of cable ties being configured to extend through the through-hole in one of the respective palm beads, wrist beads, and forearm beads and into the attachment structures on one or more of the back spine and the front spine, so as to form a customizable sized splint; wherein each of the back spine and the front spine respectively include an attachment area, each attachment area including a first orientation through-hole and recessed area and a second orientation through-hole and recessed area; wherein the first orientation is configured to allow the pair of palm beads to fit a wearer's right hand, and the second orientation is configured to allow the pair of palm beads to fit a wearer's left hand and wherein the back spine includes a back spine upper portion, a back spine lower portion, and a back spine bend between the back spine upper portion and the back spine lower portion; the back spine bend being an angle of approximately 15 degrees; the front spine includes a front spine upper portion, a front spine lower portion, and a front spine bend between the front spine upper portion and the front spine lower portion; the front spine bend being an angle of approximately 15 degrees; and the back spine bend and the front spine bend being configured so as to accommodate a wearer's wrist being immobilized at an vertical angle relative to the wearer's forearm.

2. The kit of claim 1, wherein each of the back spine and the front spine consist essentially of a thermoplastic polymer.

3. The kit of claim 1, wherein each of the back spine and the front spine consist essentially of thermoplastic polylactide, such that the back spine and the front spine may be changed in shape by a user through the application of heat.

4. The kit of claim 1, wherein the customizable size splint is configured to be adjusted in size by tightening the plurality of cable ties around the wearer's forearm and hand.

5. A customizable sized splint for immobilizing a portion of a wearer's body, comprising:

a first spine, configured to extend along a first side of the wearer's limb;

a second spine, configured to extend along a second side of the wearer's limb, the second side of the wearer's limb being opposite the first side of the wearer's limb;

each of the first spine and the second spine respectively including a plurality of attachment structures therein on an outer surface thereof;

a plurality of sets of beads, each set of beads being configured to partially surround a portion of the wearer's limb, each bead in the plurality of sets of beads including a through-hole therein; and a plurality of cables ties, each cable tie connecting the bead in each respective set of beads to the first spine and the second spine by extending through the through-hole in each bead and connecting to another cable tie at the attachment structure, the plurality of cable ties thereby connecting the first spine to the second spine so as to immobilize the wearer's limb therebetween; wherein each of the back spine and the front spine respectively include an attachment area, each attachment area including a first orientation through-hole and recessed area and a second orientation through-hole and recessed area; wherein the first orientation is configured to allow the pair of palm beads to fit a wearer's right hand, and the second orientation is configured to allow the pair of palm beads to fit a wearer's left hand and wherein the back spine includes a back spine upper portion, a back spine lower portion, and a back spine bend between the back spine upper portion and the back spine lower portion; the back spine bend being an angle of approximately 15 degrees; the front spine includes a front spine upper portion, a front spine lower portion, and a front spine bend between the front spine upper portion and the front spine lower portion; the front spine bend being an angle of approximately 15 degrees; and the back spine bend and the front spine bend being configured so as to accommodate a wearer's wrist being immobilized at an vertical angle relative to the wearer's forearm.

6. The splint of claim 5, wherein each of the first spine and the second spine consist essentially of a thermoplastic polymer, such that the first spine and the second spine may be changed in shape by a user through the application of heat.

7. The splint of claim 5, wherein the customizable size splint is configured to be adjusted in size by tightening the plurality of cable ties around the wearer's limb.

8. The splint of claim 5, wherein the wearer's limb is an arm, and the splint is configured to fit around the wearer's forearm, wrist, and hand.

9. The splint of claim 5, wherein the wearer's limb is selected from the group consisting of: an arm, a wrist, an elbow, a finger, a thumb, a leg, a knee, an ankle, and a foot.

10. The splint of claim 5, wherein each cable tie includes a head end including a one-way ratchet mechanism, and each attachment area includes a recessed area configured to allow the head end of a cable tie to fit therein.

11. The splint of claim 5, wherein each bead in the plurality of sets of beads includes a foam layer on an inner side thereof.

12. A kit for assembling a waterproof splint, comprising:

a back spine, the back spine including a first waterproof closed-cell foam layer on an inner surface thereof;

a front spine, the front spine including a second waterproof closed-cell foam layer on an inner surface thereof;

each of the back spine and the front spine respectively including a plurality of attachment structures therein on an outer surface thereof;

a plurality of sets of beads, each set of beads being configured to partially surround a portion of the wearer's limb, each bead in the plurality of sets of beads including a through-hole therein and each bead in the plurality of sets of beads including a waterproof closed-cell foam layer on an inner surface thereof; and a plurality of cable ties, each of the plurality of cable ties being configured to extend through the through-hole in one of the beads in each of the plurality of sets of beads and into the attachment structures on each of the back spine and the front spine, so as to form a customizable sized splint; wherein each of the back spine and the front spine respectively include an attachment area, each attachment area including a first orientation through-hole and recessed area and a second orientation through-hole and recessed area; wherein the first orientation is configured to allow the pair of palm beads to fit a wearer's right hand, and the second orientation is configured to allow the pair of palm beads to fit a wearer's left hand and wherein the back spine includes a back spine upper portion, a back spine lower portion, and a back spine bend between the back spine upper portion and the back spine lower portion; the back spine bend being an angle of approximately 15 degrees; the front spine includes a front spine upper portion, a front spine lower portion, and a front spine bend between the front spine upper portion and the front spine lower portion; the front spine bend being an angle of approximately 15 degrees; and the back spine bend and the front spine bend being configured so as to accommodate a wearer's wrist being immobilized at an vertical angle relative to the wearer's forearm.

13. The kit of claim 12, wherein a first cable tie in the plurality of cable ties extends through a first bead in a first set of beads of the plurality of sets of beads;

a length of the first cable tie between the attachment structures on each of the back spine and the front spine is customized in order to position the first bead adjacent to a first side of a wearer's limb;

a second cable tie in the plurality of cable ties extends through a second bead in the first set of beads of the plurality of sets of beads; and a length of the second cable tie between the attachment structures on each of the back spine and the front spine is customized in order to position the second bead adjacent to a second side of a wearer's limb, the second side of a wearer's limb being opposite the first side of the wearer's limb;

the length of the first cable tie and the length of the second table tie thereby customizing a size of the splint when worn on a wearer's limb.

14. The kit of claim 12, wherein each of the waterproof closed-cell foam layers comprises an adhesive-backed closed-cell polyethylene foam.

15. The kit of claim 12, wherein each of the beads in the plurality of sets of beads consists essentially of ABS.

16. The kit of claim 12, wherein each bead in a first set of beads of the plurality of sets of beads has a curved inner surface with a first radius of curvature configured to conform to a first portion of a wearer's appendage; and each bead in a second set of beads of the plurality of sets of beads has a curved inner surface with a second radius of curvature, the second radius of curvature being different from the first radius of curvature, such that the second set of beads is configured to confirm to a second portion of a wearer's limb that is different from the first portion of the wearer's appendage.

17. The kit of claim 12, wherein the kit includes a first set of beads, a second set of beads, and a third set of beads;

each bead in the first set of beads having a first radius of curvature on an inner surface thereof;

each bead in the second set of beads having a second radius of curvature on an inner surface thereof;

each dead in the third set of beads having a third radius of curvature on an inner surface thereof;

the second radius of curvature being larger than the first radius of curvature; and the third radius of curvature being larger than the second radius of curvature.

18. The kit of claim 12, wherein each of the back spine and the front spine consist essentially of a thermoplastic polymer, such that the back spine and the front spine may be changed in shape by a user through the application of heat.

* * * * *